(12) United States Patent
Andreiko (10) Patent No.: US 7,331,782 B2
(45) Date of Patent: Feb. 19, 2008

(54) ORTHODONTIC SUSPENSION BRACKET AND METHOD OF USE (75) Inventor: Craig A. Andreiko, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 445 days.

(21) Appl. No.: 10/734,742

(22) Filed: Dec. 12, 2003

(65) Prior Publication Data
US 2004/0157185 A1 Aug. 12, 2004

Related U.S. Application Data (60) Provisional application No. 60/432,868, filed on Dec. 12, 2002.

(51) Int. Cl.
A61C 3/00 (2006.01)

(52) U.S. Cl. ........................................................ 433/9

(58) Field of Classification Search .................... 433/8, 433/9
See application file for complete search history.

(56) References Cited

U.S. PATENT DOCUMENTS

| 3,052,027 | A |   | 9/1962  | Wallshein      |       |
|-----------|---|---|---------|----------------|-------|
| 3,460,254 | A |   | 8/1969  | Scheuer        |       |
| 4,068,379 | A | * | 1/1978  | Miller et al.  | 433/9 |
| 4,094,068 | A | * | 6/1978  | Schinhammer    | 433/9 |
| 4,186,488 | A |   | 2/1980  | Wallshein      |       |
| 4,256,455 | A | * | 3/1981  | Forster        | 433/8 |
| 4,544,353 | A | * | 10/1985 | Maurer et al.  | 433/9 |
| 4,904,188 | A | * | 2/1990  | Baurmash       | 433/215 |
| 5,110,290 | A |   | 5/1992  | Wong           |       |
| 5,263,859 | A |   | 11/1993 | Kesling        |       |
| 5,722,826 | A |   | 3/1998  | Tuneberg et al. |      |
| 5,746,593 | A | * | 5/1998  | Forster        | 433/8 |
| 6,017,216 | A |   | 1/2000  | DeLeo          |       |
| 6,071,117 | A |   | 6/2000  | Andreiko et al. |      |
| 6,749,426 | B2 | * | 6/2004 | Devanathan     | 433/9 |

* cited by examiner

Primary Examiner—Ralph A. Lewis
(74) Attorney, Agent, or Firm—Wood, Herron & Evans, L.L.P.

(57) ABSTRACT

An orthodontic appliance for attachment to a tooth with adhesive is provided that resists debonding due to impact. The appliance is provided with a compliant interface between the adhesive and the point of impact. An appliance may be provided with an orthodontic bracket suspended from a mechanical bonding base that is to be secured with adhesive to a tooth. The suspension provides compliant movement between the appliance and the mechanical bond. The movement is preferably resilient or elastic movement, but may be plastic. The movement resists fracture of the adhesive by more slowly decelerating an impacting mass, reducing forces on the adhesive. A pad attached at its outer periphery to a mesh which leaves the inner central portion of the pad free may provide the compliance, so the pad exhibits flex, suspending the bracket to move with impacting masses, absorbing energy and reducing forces transmitted to the adhesive. Compliance may also be provided by coating the bracket with elastomeric material, or coating the mechanical bonding base to which adhesive bonds. Low elastic modulus adhesive or elastic bracket tie wings can also provide the compliance. Tapered appliance surfaces, particularly facing the occlusal plane, deflect impacting objects to reduce forces.

13 Claims, 2 Drawing Sheets

ORTHODONTIC SUSPENSION BRACKET AND METHOD OF USE

This application claims the benefit of and priority to U.S. Ser. No. 60/432,868, filed on Dec. 12, 2002.

FIELD OF THE INVENTION

The present invention relates to orthodontic appliances for use in dental applications, and in particular, to orthodontic appliances, especially brackets, that are bonded to the surfaces of teeth with adhesive. The invention particularly relates to the resistance to debonding of such appliances from forces that would cause failure of the adhesive holding such appliances to a patient's teeth.

BACKGROUND OF THE INVENTION

Millions of dollars are spent each year in trying to improve a smile, align teeth and/or correct a periodontal defect. Tooth malocclusion and other periodontal defects are typically caused during periodontic development and by oral deformities, such as extra teeth and the like. Periodontic defects can lead to further problems if left uncorrected or unrepaired. For example, malocclused teeth may lead to problems associated with biting and the chewing of food as well as to problems related to jaw structure and jaw movement, and to the development of incoming permanent teeth. Accordingly, periodontic defects need to be corrected. In addition, young persons, particularly in their teens and twenties, are often unhappy with periodontic imperfections or problematic teeth, particularly if it affects their smile or appearance in general, and desire to have the problems corrected.

In the field of orthodontics, techniques to correct such problems include applying or attaching orthodontic appliances across the problematic areas, and in particular, across malocclused teeth to straighten or correct their alignments relative to each other and to the patient's skeletal structure. To this end, orthodontic appliances, such as brackets, buccal tubes and the like, are adhered directly to the surfaces of the teeth to transmit corrective forces from orthodontic archwires or other elastic devices to the teeth for corrective purposes. The orthodontic appliance that is most commonly attached to a tooth is the orthodontic bracket. The most common orthodontic bracket in use includes a rectangular slot to support an archwire and tie wings or other ligating structure for use in tying the archwire to the bracket. Such bracket structure is generally provided with a base or other tooth engaging structure with which the bracket is adhered to the tooth surface.

In orthodontics, the term 'appliance' may be used to refer to an entire assembly of components, including brackets, archwires, buccal tubes, etc., that are used to treat patients. The term 'appliance' may also be used to refer to the individual components of such assemblies, including the individual brackets and archwires, etc. Similarly, the term 'bracket' is used to refer to archwire supporting structure that usually contains an archwire slot and tie wings, which structure may be fixed to a bonding base, pad or other structure that supports the bracket on a tooth. The term 'bracket' may also apply to an entire device that includes the archwire supporting structure as well as bonding base structure to which the archwire supporting structure may be fixed.

More particularly, a bracket-type appliance generally has a bonding surface adapted to bond with adhesive to the surface of a patient's tooth. This surface may be a surface on the archwire support structure itself or may be a surface on a pad, which usually has a larger perimeter than the archwire support structure, and which is either formed integrally with the archwire support structure or as a separate sheet to which the archwire support structure of the bracket is fixed. Such a pad has the archwire support structure or bracket on one side thereof, the other side of the pad providing the bonding surface for bonding to a tooth. With either configuration, the bonding surface is referred to as a bonding base. The term 'base' in relation to a bracket is therefore used to refer to various parts of the structure between the archwire support and the adhesive that holds the bracket to a tooth.

The bonding surface to which adhesive is applied often includes structural elements, such as a mesh or other highly textured structure, that presents undercuts or other interlocking features and forms a mechanical or interlocking bond with adhesive that has filled the voids in the structure and hardened, thereby assisting in bonding the bracket to the tooth to which the adhesive is applied. Such a bonding surface is referred to as a 'mechanical bonding base'. Adhesive is generally applied to a bonding surface of a tooth, with the orthodontic appliance being pressed onto the adhesive. The adhesive compound is then cured to create a chemical or mechanical bond between the adhesive and the tooth and a chemical and/or mechanical bond to the bonding base, pad, or other engaging structure on the bracket. In a similar fashion, each of a plurality of orthodontic appliances is adhered to the surface of a tooth and interconnected with each other by an archwire or otherwise to form the appliance.

In use, orthodontic appliances are subjected to a variety of forces exerted upon the appliance in addition to forces exerted on brackets by archwires. More particularly, force and energy are exerted against appliances when objects contact orthodontic appliances including brackets that are adhered to tooth surfaces. Such contacts result in forces that are conveyed or transferred through the bracket directly to the adhesive bond securing the appliance to the tooth. When the force exceeds the limitations of the adhesive bond, the bond may fracture, completely break, or totally fail resulting in the bracket being dislodged or debonded from the tooth. A rather small amount of contact may be all that is necessary to fracture the adhesive.

The loads that cause the debonding of orthodontic appliances from teeth most often come from the occlusal direction and are generally normal to the occlusal plane. Such loads that produce forces capable of causing the bond to crack or otherwise fail, and the appliance to thereby debond from the tooth surface, are typically exerted upon the appliance during normal, everyday activity. Mere eating and chewing of food, grinding of teeth, and other masticatory activity in the mouth may exert large forces on the appliance and, in particular, forces sufficient to cause the bracket adhesive to fail. Often it is the closing motion of the jaw that applies the forces against intervening hard objects against the teeth and appliances bonded to the teeth.

Orthodontists have experienced that a substantial percentage of brackets fail during treatment. The percentage may be in the area of about ten percent. With approximately two million orthodontic treatments being started each year in the United States, with each using typically twenty brackets per case, and with treatment lasting on the average about two years, a substantial number of failures, approximately forty million, may be expected to occur each year. With ten thousand practicing orthodontics in the United States, each orthodontist might expect, on average, four hundred failures per year. Estimating the cost to the orthodontist of each bracket failure at about seventy-five dollars, the loss, in time or money, to the average orthodontist may be calculated at about $30,000. Accordingly, bracket failure is a major problem that must be addressed.

To address the problems of the failures of adhesives between orthodontic appliances and teeth, the prior art has focused on the forces involved in bond failure. Such forces are traditionally analyzed by tests designed to measure static loads on the appliance. To resist these forces and to prevent dislodging of the orthodontic appliance from the tooth, the prior art has focused on strengthening the bond between the appliance and the tooth.

For example, U.S. Pat. No. 5,071,344 to Wong teaches an orthodontic appliance having a bracket with a base portion for attachment to the tooth. The base portion has a substantial monolayer formed of substantially uniform size particles. The particles provide a larger contact surface for bonding to the adhesive to generate a stronger bond.

U.S. Pat. No. 5,110,290 to Wong teaches an orthodontic appliance having a ceramic engaging surface for attachment to the tooth. This patent discloses the use of a wire mesh between the ceramic engagement surface of the base portion of the appliance and points of attachment on the tooth. The wire mesh has a plurality of openings through which the adhesive passes to allow for a stronger mechanical bond between the adhesive and the mesh.

U.S. Pat. No. 5,722,826 to Tuneberg teaches a bonding pad for an orthodontic attachment to be bonded to a tooth, including a foil or plate having a photoetched surface, and a layer of mesh material diffusion bonded to the photoetched surface. The photoetched surface provides a secondary bond interlock, while the mesh provides a primary bond interlock, thereby increasing the strength of the bond between the bonding pad attached to a bracket and the tooth.

While prior art orthodontic appliances have improved the bonding strength between the orthodontic appliance and the tooth, such improvements are not without their drawbacks. For instance, stronger bonds can concentrate impacts and forces and potentially lead to fracture of the adhesive and/or the bracket-base, and thereby dislodge the appliance. Further, stronger, more secured mechanical bonds between the bracket and the mesh generally concentrate this force to specific locations or points in the adhesive. This concentration of force leads to a greater likelihood of bond failure and dislodging or even debonding of the appliance upon smaller, less energetic contacts or impacts. In effect, some of the increased force resistance provided by the stronger bond is countered by the concentration of the impacting force.

Further, strengthening the bond can have deleterious effects. With a stronger bond between the bracket and the tooth, if the bracket dislodges upon impact, it is more likely to remain bound to the adhesive layer thereby dislodging or tearing with it a portion of the underlying enamel from the surface of the tooth. Further, a stronger bond renders the appliance more difficult for an orthodontic practitioner to remove without adverse effects up to and including the pulling of tooth enamel from the tooth. Torn enamel not only causes pain to the patient, but also requires a repair which is both inconvenient and costly.

Consequently, the prior art has also attempted to develop orthodontic appliances designed to reduce such tearing and pulling of tooth enamel when they are debonded. U.S. Pat. No. 5,263,859 to Kesling teaches an improved, flexible bonding pad or base for an orthodontic ceramic bracket to facilitate debonding of the bracket from the tooth and a method of debonding. This base or pad is formed of relatively flexible material to allow the application of compressive and buckling force, with dental pliers, to break the bond between the base and the tooth for removal of the bracket therefrom. Removal of the bracket is accomplished without subjecting the bracket to such forces capable of fracturing the bracket.

U.S. Pat. No. 6,017,216 to Deleo, teaches an orthodontic bracket apparatus, for attachment to a tooth, consisting of a flexible attachment pad having a pair of brackets permanently mounted on adjoining areas at one side of the pad and spaced in relation to each other. This side-by-side arrangement of the brackets is intended to provide easy arcuate adjusting movement of each bracket with respect to the other bracket so as to obtain a tighter fit of the entire pad to the surface contours of the tooth to which the apparatus is affixed.

While the prior art has proposed solutions which strengthen the chemical or mechanical bond adhering the orthodontic appliance to the tooth surface, these methods, however, have done so at the expense of making the appliance more difficult to remove once the teeth have been corrected, and increase the risk of tearing and removing a portion of the enamel of a tooth when the appliance is removed by the orthodontic practitioner or when it is unintentionally debonded due to impact. Consequently, the person wearing the orthodontic appliance faces additional problems, such as added cost, repair and inconvenience.

Thus, there is a need to provide an orthodontic bracket or other appliance for attachment to a tooth that will resist commonly encountered events during normal masticatory activity and removal practices without having the undesirable side effects and drawbacks of the prior art orthodontic appliances discussed above.

SUMMARY OF THE INVENTION

A primary objective of the present invention is to reduce the likelihood of an orthodontic appliance to fail.

The present invention is based in part on a determination, neglected in the prior art, that impact, as distinguished from static force, is a major contributor to adhesive bond failure between orthodontic brackets, or other appliances, and teeth.

According to the principles of the present invention, orthodontic appliances are configured or mounted on the teeth of a patient in such a way as to reduce the likelihood that forces will develop from impact that will debond an appliance from a tooth or otherwise result in the failure of the appliance. In particular, the invention provides orthodontic appliances that are more resistant to impact that may be typically encountered during normal, everyday activity than are the orthodontic appliances of the prior art.

According to various embodiments of the invention, orthodontic appliances are configured or mounted on teeth in such ways as to absorb, deflect or otherwise manage the energy imparted to appliances or teeth from impact that would result in the application of forces on appliances or their interfaces with teeth.

In certain embodiments of the invention, material or structure is provided between the impacting source and the tooth that dissipates or stores or otherwise absorbs energy of an impact. Such absorption may be provided in such a way that the appliance yields to an impacting object, either plastically or elastically, permanently absorbing the energy or returning the energy to the object. The yielding is provided by allowing movement in the area of impact that exceeds that provided with appliances in the prior art.

In other embodiments of the invention, in the alternative or in addition to energy absorbing features, energy may be deflected by a profile, inclination or other configuration of surfaces of the appliance so that at least some of the energy of impact is redirected or repelled from the object, thereby reducing the amount of energy to be absorbed or that could result in high reacting forces that would be damaging to the appliance or to its bond to the teeth.

In accordance with one embodiment of the present invention, an orthodontic appliance is provided having a bonding base or other bonding surface configured to allow movement of the appliance with respect to the adhesive interface between the appliance and the tooth when the appliance is subjected to impact. The appliance so provided better resists not merely static, but also dynamic factors that tend to cause the debonding of appliances from teeth. Accordingly, without the bond between the appliance and the tooth necessarily being made stronger, the appliance is less susceptible to debonding, because it, by its design, subjects the appliance's adhesive interface with the tooth to lower forces when the appliance is subjected to a given impact from an external object.

In accordance with certain principles of the present invention, an orthodontic appliance is provided that responds in a flexible or otherwise compliant manner when subjected to impact. The appliance resists impact by providing a degree of motion between the surface of the appliance that is exposed to impact from external objects and the adhesive or the surface of the tooth.

In certain embodiments of the invention, an orthodontic appliance is provided comprising a bracket and having a bonding surface that is suspended on the bracket structure in such a way as to resist impact and minimize dynamic forces to the adhesive interface that might result. Embodiments include, for example, suspended bonding base structure, such as a mesh or other textured layer, for providing mechanical bonding of the bracket with a tooth surface through the use of an adhesive. The bonding base structure is attached to the bracket structure so as to allow, upon impact during use, the bracket and the bonding base to move compliantly relative to one another. This compliant movement, in effect, absorbs the energy of impact thereby resisting transmission of a high force of impact from the bracket to the adhesive. In this fashion, the present orthodontic appliance provides deceleration of impacting objects over the distance of the relative compliant movement, thereby decreasing the force transferred to the adhesive between the bonding base and the tooth. In addition, the resiliency or other compliant motion serves to redistribute the force vectors more favorably and more evenly across the adhesive-structure interface, thus increasing the impact resisting ability of the appliance and reducing the potential for an impact to dislodge the appliance from the tooth.

In certain embodiments of the invention, the bonding base comprises an outer peripheral portion and an inner central portion. Resilient or damping properties are achieved by attaching the outer peripheral portion of the bonding base to the periphery of the archwire support structure or to a surface of a separate component, such as a pad, to which the archwire support structure is fixed. The inner central portion of the bonding base is left substantially free from attachment. For greater strength and impact resistance, the outer peripheral portion of the bonding base may be attached at multiple points to the outer peripheral portion or around the entire periphery of the pad or base of the archwire support. In another aspect of the invention, the pad or base may comprise different regions, each having an outer peripheral portion, one or more of which may be attached to the structure for resilient or otherwise compliant movement.

Advantageously, the bonding base in certain embodiments is preferably a continual surface to provide uniformity in attaching the base structure to the outer peripheral portion of the pad or bracket base, and is either flat or slightly curved to conform to the curvature of a tooth. More advantageously, the bracket base or pad may comprise a thin metal sheet, such as foil for example, to which the bonding base structure, such as a stainless steel mesh layer for example, is attached in a multitude of points around its outer peripheral portion. Such foil may behave like a smooth rigid surface, which generally provides the advantages of strength and non-adhesion to the underlying adhesive. The bonding structure may be secured to the outer peripheral portion of the bracket base or pad by conventional techniques. Where these parts are metal, the bonding base and bracket base are preferably welded together at their perimeters.

Impact resistance may also be enhanced, according to certain principles of the invention, by having the orthodontic appliance generally comprise an impact resistant material. For example, a metal bracket allows for deceleration of an impacting mass by virtue of the flexibility and elasticity of the metal itself, while also being sufficiently firm and inexpensive. Where the bonding base is fixed to a bracket's metal pad, such as foil, or to a pad that is of some other material, for example plastic, having resilient or elastic properties, the flexibility of the pad between the attachment point of the bracket and the pad perimeter provide compliant, and particularly resilient, movement.

Alternatively, a bracket or other appliance may be made of a ceramic material which is more rigid than metal. Certain principles of the invention may be applied to such brackets by providing such a bracket with a pad of metal or other material, or a bonding interface, that is more resilient than ceramic, or by providing the outer surface of the bracket with a polymer or other coating of a resilient or otherwise compliant material that is amenable to impact. Still further, the bracket may be made of plastic, which may be provided with features of the present invention.

Bonding base structure is advantageously a mesh, such as a grid of woven wire, so as to provide adequate surface area to mechanically bond the bracket to the tooth. Such mesh is particularly suitable for metal brackets. Mechanical bonding base layers may be configured with beads, chards, fibers or other intricate structure that will provide undercuts or voids which will shape the adhesive, once it hardens, into interlocking structure that forms a mechanical bond between the adhesive and the appliance. Different structures may be more suitable for different materials.

Yet another aspect of the invention provides a method of constructing the orthodontic appliance described above and attaching the appliance to a tooth. To this end, the bracket and bonding base structure are made by being attached together in such a way as to form a compliant orthodontic appliance which is bonded and secured to the tooth surface through an adhesive and more resistant to impact than appliances of the prior art.

An embodiment of an energy absorbing orthodontic bracket is a bracket having resilient or elastic tie wings, such as may be made of a spring metal or an elastomeric polymer material. The wings may be configured to flex, particularly in a gingival-occlusal direction.

Another embodiment of an energy absorbing appliance is one having a wire mesh or other hard mechanical bonding base that is provided with a layer of deformable material. For example, in one embodiment, the wire mesh is sprayed or otherwise coated with an elastic polymer material, which forms a layer between the wire mesh and an adhesive with which the appliance is bonded to a tooth. The elastic material flexes enough to reduce the force needed to decelerate a load, and dissipate the energy, of an impacting object.

A further embodiment of an energy absorbing appliance mounting method involves the use of an adhesive that has a substantially lesser elastic modulus than adhesives that are used in the prior art for bonding the appliances to teeth. By providing adhesive with a higher elongation-to-failure than adhesives previously used for this purpose, substantially lower forces may result from impacting objects, so that such more highly elastic adhesives, even if they have lower yield strengths, would be less likely to fail under a given impact load.

An example of an energy deflecting appliance is a bracket or other appliance having tapered surfaces, particularly facing the occlusal side thereof. Such appliances are configured to present minimal edges or surfaces that may be normal to impacting loads from the occlusal plane or that would otherwise tend to oppose or resist the motion of an impacting object. Rather, the tapered surfaces and minimal surfaces would allow the impacting object to slide or be deflected from the appliance, thereby avoiding a sudden and large reactive tensile force that would be required to decelerate the object.

These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to explain the invention.

DETAILED DESCRIPTION OF THE DRAWINGS

As used herein, the term 'orthodontic appliance' refers to a device which is adhered to a tooth surface for moving teeth to, or holding teeth in, particular positions. Non-limiting examples include orthodontic brackets, buccal tubes and the like. As used herein, the term 'compliant' is intended to refer to flexibility, resiliency and to the ability to otherwise resist response to impact, either elastically or plastically.

Figure 1:
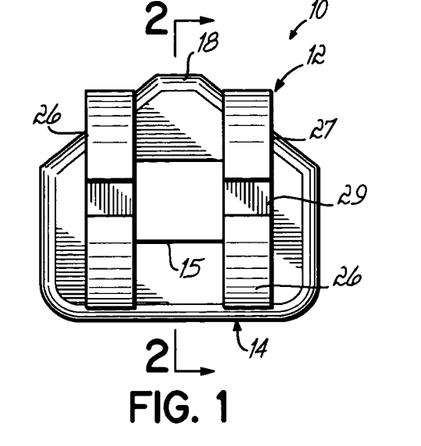
FIG. 1 is a front view of an exemplary orthodontic appliance in accordance with the principles of the present invention.
Figure 2:
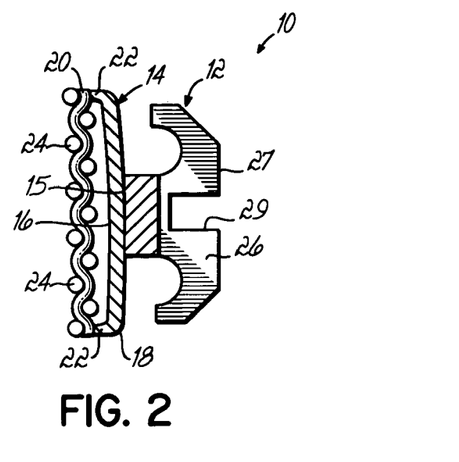
FIG. 2 is a cross-sectional view taken on line 2-2 of the exemplary orthodontic appliance illustrated in FIG. 1.

With reference to FIGS. 1 and 2, there is shown, in front view and cross-sectional view respectively, an exemplary orthodontic appliance 10, such as a bracket. The appliance 10 includes archwire support structure 12 which is fixed to a pad 14 through a bracket base 15. The pad 14 has a bonding base or bonding structure 20 attached thereto in such a way as to provide compliancy between the archwire support structure 12 and the bonding structure 20 upon impact. In the exemplary embodiments illustrated in FIGS. 1-5, the bonding structure 20 is in the form of a mesh 20 as illustrated, however, the bonding structure 20 is not limited to mesh, as will be further discussed herein.

Figure 4:
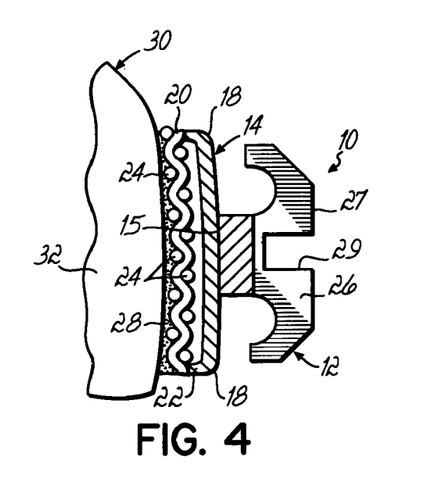
FIG. 4 is a cross-sectional view of the exemplary orthodontic appliance illustrated in FIG. 1 attached to a surface of a tooth.

As shown in FIG. 2, the pad 14, is a component separate from the base 15, and is attached to the mesh bonding structure 20 at one or more points 22. The pad 14 may be firmly secured to the base 15 of archwire support structure 12 by conventional methods, such as by sintering or diffusion bonding. Also, more traditional methods such as welding or soldering may be used. Upon impact, the archwire support structure 12 and pad 14 move in unison. The attachment points 22 between the pad 14 and the mesh bonding structure 20 are configured to provide resiliency and allow compliant movement of one of either the pad 14 or the mesh 20 relative to the other. The movement of the pad 14 and the corresponding archwire support structure 12 being independent of the mechanically bonded mesh 20 allows the orthodontic appliance 10 to more slowly decelerate an impacting mass, thereby resisting transmission of impacting forces and reducing the amount of the impacting forces transmitted to the underlying tooth surface through the attaching adhesive (FIG. 4). To this end, the ability to resist debonding or detaching of the appliance 10 from the tooth surface upon impact of an object with the surface of a bracket, archwire, or other appliance surface is improved over orthodontic appliances of the prior art.

The archwire support structure 12 may be a conventional bracket of a type known in the prior art for use in orthodontic appliances. Accordingly, the archwire support structure 12 may include a rigid archwire support 27 having an archwire slot 29 therein adapted to support an archwire and tie wings 26 adapted to receive bands or other ligatures (not shown), which wrap around the wire and tie wings to thereby form interconnections among more than one orthodontic appliance 10.

Appliance 10 may be made of materials conventionally used in the field of orthodontic appliances and applications. In various embodiments of the invention, the appliance 10 comprises materials selected from a metal, a ceramic, and a plastic. Advantageously, for many applications, the appliance 10 is formed of metal. Metal is more flexible than ceramic and less expensive than both ceramic and plastic. In addition, metal uniformly transfers and distributes impacting forces to the attached mesh 20 and to the mechanically bonded adhesive 28 (FIG. 4). Plastics absorb more force from the impact than metal or ceramic, however, plastic does not evenly transmit the force to the underlying bonded adhesive 28. Persons of ordinary skill in the art readily understand that the materials themselves, by virtue of their very nature, may absorb some of the impacting forces thereby providing a source of deceleration for the impacting object.

The appliance 10 may, in an alternative to the structure described above, include an integral surface, such as that of the base 15, adapted for attachment to the mesh 20 at one or more points 22. For this purpose, the base 15, as with a pad 14, may be formed of the same material as support structure 12 or of a different material. For example, metal brackets advantageously have suitable metal surfaces for use as a base 15. Both the pad 14 and the base 15 may advantageously be a surface that is generally flat or has a curvature conforming to that of the tooth to which it is to attach, and may comprise a metal sheet covering or coating the surface.

For example, in one embodiment, the base 15 comprises a thin metal sheet that may be characterized as a fairly rigid foil. The foil may form the entire base 15 or only desired regions or distinct points of the base 15 where mesh 20 is to be attached. In another embodiment, the pad 14 comprises a foil. In yet another embodiment, the pad 14 is a sheet of foil. Foil is a thin sheet of metal which is sufficiently stiff to resist buckling under stress (FIG. 4). It is also inexpensive, lightweight and commonly used in the industry. More particularly, such foil tends to be sufficiently rigid wherein, upon an impact of force, the foil's rigidity resists folding or bending or otherwise being crumpled. In addition, such foil generally withstands energies and forces greater than the force limitations of the corresponding underlying adhesive. Further, such foil does not particularly adhere to the adhesive, thereby enhancing compliancy between the pad 14 or base 15 and the adhesive-mesh 20 bonding layer. Where the pad 14 is a foil, it may be attached to the base 15 by welding or soldering. The pad 14 of the present invention, however, is not limited to foil, as other metals, ideally thin, light weight metal sheets, or other materials may also be used as the pad 14 for attachment of the archwire support structure 12 to the mesh 20.

Together, the pad 14 and the attached mesh 20 generally provides the capability for mechanical bond between the orthodontic appliance 10 and the tooth. As described earlier, it is a bonding structure, or structure illustrated in the exemplary embodiment shown in FIG. 2 as a mesh 20, which provides the mechanical bonding. To this end, the structure may be any size, shape, form and/or material suitable to provide increased surface area for mechanically bonding the pad 14 or the base 15 to the adhesive. For instance, the structure, without limitation, may be a solid sheet-like surface with projections to provide mechanical bonding. Optionally, the structure may comprise a polymer fibrous material or a solid metal. It is beneficial for the structure to be flexible for bonding to an uneven tooth surface. In the exemplary embodiment illustrated in FIG. 2, the structure is a mesh 20, such as a wire mesh or screen. This mesh 20 comprises a series of parallel filaments 24, cross-woven perpendicular to one another, to form the final cross-woven pattern illustrated. Thus, the term 'structure' as used herein is not limited to a mesh 20 and is used broadly to include any structure or device capable of providing a mechanical bond between the appliance 10 and a tooth (not shown) and being attached in more than one point to the pad 14 or to the base 15 of the archwire support structure 12.

In accordance with principles of the present invention, the attachment between pad 14 and mesh 20 provides compliant movement between one another upon impact. To this end, and with reference to FIG. 2, pad 14 comprises thereon at least one inner central portion 16 and an outer peripheral portion 18 in surrounding relation to the inner central portion 16. Advantageously, the inner central portion 16 and outer peripheral portion 18 are one contiguous surface. More advantageously, the inner central portion 16 is completely surrounded by the outer peripheral portion 18 (FIG. 1). One or more points 22 on the outer peripheral portion 18 are attached to the mesh 20, while the inner central portion 16 is substantially free from attachment to mesh 20. As used herein, the term 'substantially free' with reference to points of attachment between the pad 14 and the mesh 20 is intended to refer to very limited number of attachment points, if any at all, relative to the multitude of possible points at which attachment may occur.

Advantageously, the outer peripheral portion 18 of the pad 14 is attached in more than one point 22 to the mesh 20 and more advantageously, in a substantial number of points 22 spanning the circumference of the outer peripheral portion 18 of the pad 14. The embodiment illustrated in FIG. 1 has the outer peripheral portion 18 of pad 14 continually attached to the mesh 20 leaving the inner central portion 16 relatively free from any such attachment. Leaving the inner central portion 16 of the pad 14 relatively free from attachment to the mesh 20 is important as the compliancy of the orthodontic appliance 10 generally improves with an increase in area of unattached inner central portion 16. Similarly, the base 15 may include regions analogous to the inner central portion 16 and the outer peripheral portion 18 of the pad 14 described above. Where the archwire support structure 12 is attached directly to the mesh 20, i.e., without attachment through an intermediary pad 14, compliancy between the archwire support structure 12 and the mesh 20 can be achieved through the patterns of attachment described above.

Figure 3:
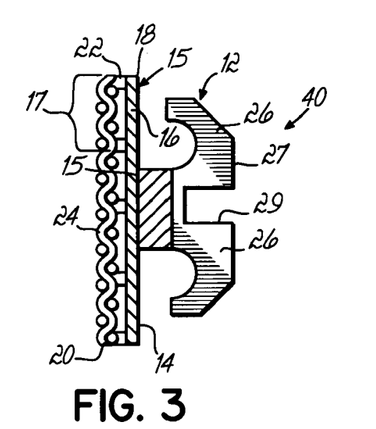
FIG. 3 is a cross-sectional view of a second exemplary orthodontic appliance in accordance with the principles of the present invention.

With reference to FIG. 3, there is shown, in cross-sectional view, a second exemplary orthodontic appliance 40 illustrating another aspect of the present invention. As shown, the pad 14 may include a multitude of selected regions or individual areas 17, wherein each region or area 17 has an inner central portion 16 surrounded by an outer peripheral portion 18. For example, and as shown in FIG. 3, a single area 17 may comprise two or more filaments 24 between successive points of attachment 22 on the outer peripheral portion 18 of the pad 14. As shown, the outer peripheral portion 18 includes attachment points 22 where the pad 14 is attached to the mesh 20 while the inner central portion 16 of the area 17 remains unattached to the filaments 24 of mesh 20. Similarly, as shown, pad 14 may comprise four such areas 17, each of which are attached to the mesh 20 in the above described fashion. The present invention is not so limited, however, and fewer than all the areas 17 on the pad 14 may be attached to mesh 20 in the manner described above. Each individual area 17 provides compliance between the archwire support structure 12 and mesh 20. Thus, each area 17 contributes to the resistance of the orthodontic appliance upon impact.

With reference to FIG. 4, there is shown, in cross-sectional view, the exemplary orthodontic appliance 10 illustrated in FIG. 2 attached to a surface 30 of a tooth 32. While orthodontic appliance 10 may be conventionally secured to the surface 30 of a tooth 32, such as for example, using suitable adhesive polymers, glues, and the like for creating a chemical bond, FIG. 4 illustrates a mechanical bond provided with an adhesive 28 previously placed on and adhered to the filaments 24 of mesh 20 to secure the appliance 10 to the surface 30 of a tooth 32. The surface 30 may be a smooth surface, an even surface, or an uneven surface depending upon the particular problem and shape of the tooth 32. Regardless of surface 30 contours, the appliance 10 is mechanically bound to the surface 30 via mesh 20 and adhesive 28. Adhesive 28, as shown, seeps through the filaments 24 of mesh 20 to maximize bonding surface area as previously discussed. Adhesive 28 generally does not adhere to foil or other similar metal based sheets covering the outer peripheral portion 18 of base 15.

Figure 5:
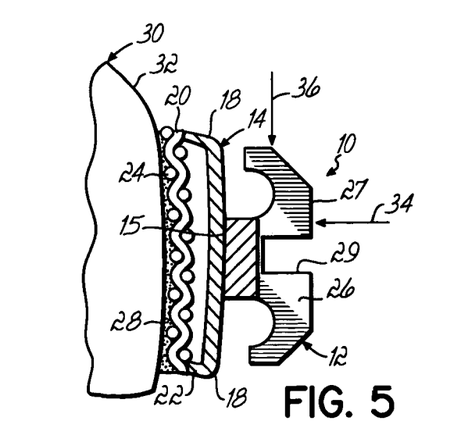
FIG. 5 is a cross-sectional view of the attached orthodontic appliance illustrated in FIG. 4 impacted by tensile and shear forces.

With reference to FIG. 5, there is shown in cross-sectional view, the attached orthodontic appliance 10 illustrated in FIG. 4 impacted by tensile and shear forces. Depending on the type of oral activity, different forces impact the orthodontic appliance 10 from different directions. For example, the appliance may be subject to a static load force, or shear force 34, applied to the appliance 10 at a horizontal angle. In addition, the appliance 10 may be subject to a dynamic load or force, commonly know as tensile force 36, applied to the appliance 10 at an angle perpendicular to the mechanically bonded adhesive 28 and tooth surface 32, often due to mastication or mandibular strain. Tensile forces 36 tend to promote failure greater than shear forces 34 and create the greatest strain on the orthodontic appliance 10 and, therefore, do the most damage to the appliance 10. Objects impacting the appliance 10, and particularly the archwire support structure 12 or the archwire, parallel to the tooth surface 30 often exert the most damaging tensile force due to the summation of force vectors in the appliance 10. Beyond the everyday oral activity, additional shear and tensile forces are generally applied to the appliance 10 by the orthodontist during removal of the orthodontic appliance 10. In practice and every day routines, the orthodontic appliance 10 may encounter forces in the range of about 7,500 psi to about 11,500 psi at which the typical mechanical bond will fail. Further, most, if not all, of the chemical and mechanical bonds of the prior art between the bracket base 14 and the tooth 32 may break or fail under lesser deceleration forces, and forces commonly encountered in daily activity.

As shown by the arrow in FIG. 5, tensile forces 36 tend to cause the appliance 10 to pull away from the tooth surface 30, often resulting in a tear or rip of either the archwire support structure 12, the pad 14, the mesh 20 or the enamel on the surface 30 of the tooth 32 to dislodge the appliance 10. The compliant pad-mesh attachment provides optimal resilient movement of the archwire support structure 12 relative to the bonded mesh 20 thereby less rapidly decelerating the object, with respect to the time and distance to reduce the object's velocity, greater then that of the appliances of the prior art. Upon such an impact, a portion of the tensile force(s) 36 and energy are absorbed by the archwire support structure 12 causing it to momentarily or permanently suspend from the mesh 20, as illustrated, without transferring the full force of deceleration onto the mesh 20 and adhesive bond between the mesh 20 and the tooth surface 30. The degree of suspension will determine the degree of resilient or plastic movement of the archwire support structure 12 relative to the mesh 20. By virtue of the ability of the archwire support structure 12 to suspend from the mesh 20, the present invention increases the impact resistance of the appliance 10 to forces beyond those at which appliances of the prior art would fail. Accordingly, the present appliance is able to withstand higher impact while reducing the maximum forces resulting therefrom, thereby minimizing the risks of failure and breakage of the archwire support structure 12, pad 14 and mesh 20 or tearing of the enamel from the surface 30 of the tooth 32.

Without limiting deceleration, the appliance 10 generally transfers most, if not all, of the impacting energy directly to the mechanically bonded interface between the mesh 20 and the adhesive 28. As a result of such transfer, the adhesive 28 may tend to fracture if it cannot absorb the energy, and ultimately dislodge or debond the appliance 10 from the surface 30 of the tooth 32. Depending upon the force involved, and extent of fracture, the debonding may cause a loss of the underlying tooth enamel, thereby requiring repair, health risks, and/or causing pain to the person. However, it is believed that by decelerating the impacting object, the amount of force transferred to the underlying mechanical bond is minimized, thereby reducing the risks of adhesive fracture or failure and debonding of the appliance 10 from the tooth 32. To this end, and in accordance with the principles of the present invention, the orthodontic appliance 10 provides more resistance to impacting forces than the appliances of the prior art. Even a small amount of deceleration of an impacting object may suffice to prevent dismemberment of the appliance 10 from the tooth 32. Persons of ordinary skill in the art appreciate that the level of compliancy or flexibility of the pad 14 or the bracket-base 15 relative to the mechanically bonded mesh or bonding structure 20 will depend upon the level of attachment to the outer peripheral portion 18 and the level of non-attachment to the inner central portion 16 of the pad 14 or base 15 thereto. Further, with reference again to FIG. 3, the number of regions 17 and the location of each region 17 on the pad 14 or base 15 having this outer peripheral portion 18 attached to the mesh 20 will influence the level of compliant movement and the total amount of impact resistance provided by the appliance 10.

Resistance to impact may also be accomplished or enhanced in yet a further aspect of the present invention. For example, the archwire support structure 12 may be coated with a flexible material (not shown), such as a rubber or other compliant polymer, to provide initial deceleration of the impacting object. Such a coating is particularly useful for ceramic brackets 12, which may otherwise be difficult to attach via a mechanical bond to the tooth 32.

Figure 6:
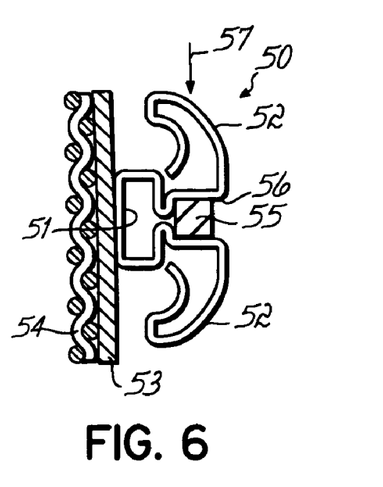
FIG. 6 is a cross-sectional view of an alternative embodiment of the appliance of FIG. 1.

FIG. 6 illustrates, in cross-sectional view, an alternate embodiment of an impact absorbing orthodontic appliance in the form of a bracket 50 having elastic tie wings 52 formed of a sheet of spring metal. A portion of the spring metal integral with the tie wings 52 forms a bracket base 51 that is welded to a pad 53 to which is welded a mesh bonding structure 54 in a conventional manner. The wings 52 are biased toward each other and against an archwire 55 mounted in an archwire slot 56 between the wings 52. When subject to impact from the occlusal plane in the direction illustrated by the arrow 57, the occlusal set of wings 52 deflects gingivally against the archwire 55, which transmits force against the gingival set of wings 52, causing them also to deflect gingivally. This deflection decelerates the impacting load sufficiently gradually to greatly reduce the force transmitted to adhesive between the mesh 54 and the tooth to which the bracket 50 is bonded.

An alternative embodiment of the invention involves the use of an otherwise conventional bracket with an extra resilient adhesive, that is, with an adhesive that has a substantially greater elongation-to-failure or substantially lower modulus of elasticity. Rubber cement is one example. Such an adhesive need not necessarily have a greater strength than conventional adhesive, but will yield more under the force applied and thereby require substantially more energy before the adhesive fails.

For example, conventional adhesives are provided in different elasticities, typically one that provides one percent elongation-to-failure and another that provides three percent elongation-to-failure (ETF). Both such adhesives may have the same yield strength, and if so, the adhesive with 3% ETF will absorb three times the energy before failure than the adhesive with the 1% ETF. According to this embodiment of the present invention, an adhesive with 3% ETF is provided. Such an adhesive will absorb substantially more energy before failure than conventional adhesives. In addition, even if provided with a significantly lower yield strength than conventional adhesives, the force that results from a given impact will be considerably less than with conventional adhesives, thereby reducing the likelihood of failure of the adhesive from impact.

Preferably, an adhesive is provided with a modulus of elasticity of 2800 MPa. This compares with typical moduli of 4700 MPa for conventional adhesives. Such low modulus adhesives can be made by modifying formulations of conventional adhesives by methods known in the art.

Figure 7:
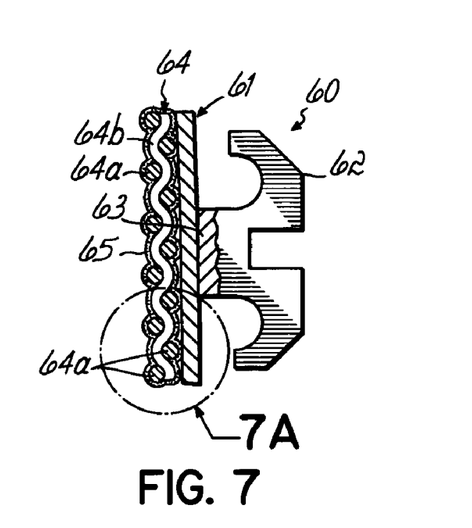
FIGS. 7 and 7A are cross-sectional views of an additional alternative embodiment of the appliance of FIG. 1.

Another embodiment of the invention is illustrated in FIG. 7, in which an orthodontic appliance 60, such as the bracket 10 of FIG. 1, is provided. The appliance 60 includes an archwire support structure 62 fixed to a pad 61 through a bracket base 63. The pad 61 has a bonding base or bonding structure 64 welded or otherwise secured thereto in a conventional manner. The bonding structure 64 may be in the form of a mesh as illustrated or other mechanical bonding structure to which adhesive is applied. The structure 64, if mesh, may be of woven stainless steel wire. As shown in more detail in the enlarged FIG. 7A, the mesh may include horizontal wires 64a and vertical wires 64b, welded to the pad 61. The wire is, conventionally, 0.1 millimeter (mm) in thickness.

Figure 7A:
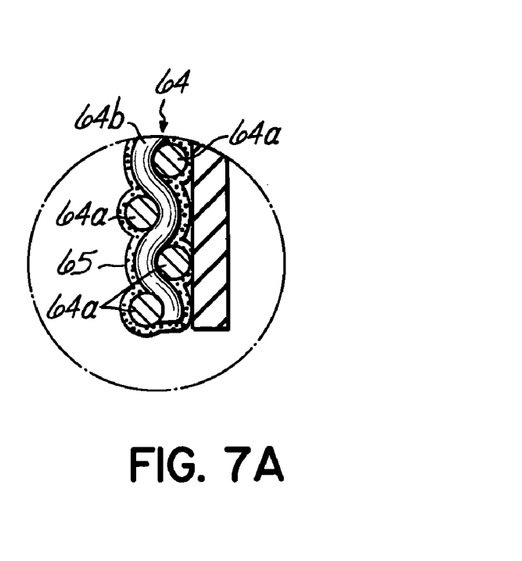

According to this embodiment of the invention, the wires 64a, 64b are sprayed or otherwise coated with a thin layer 65 of a rubber-like elastomeric material, for example, 0.003 mm thick, resulting in a coated wire diameter of, for example, 0.106 mm, of which 0.1 mm is steel and 0.006 mm is low modulus elastic material. Adhesive (not shown) surrounds the coated wire. When the appliance 60 is subjected to impact at its tie wings, for example, the force that is transmitted through the coating 65, the coating compresses on one side of the wire 64 and stretches on the other side of the wire 64 so that the pad 61 moves up to a few thousandths of a millimeter relative to the tooth due to deformation of the coating 65. This motion absorbs the energy of the impact and produces substantially less force on the adhesive than without the coating, thereby reducing the likelihood that the adhesive will fail.

Figure 8:
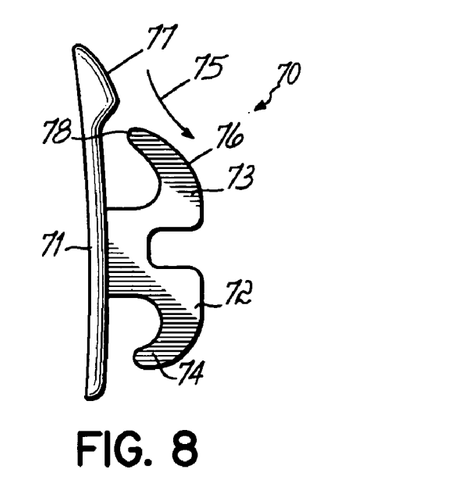
FIG. 8 is cross-sectional view of another feature of the present invention.

FIG. 8 illustrates a further embodiment of the invention in which an orthodontic appliance 70 is configured so as to deflect impact by providing surfaces that are shaped so that objects are not abruptly stopped upon contact with the surface of the appliance 70. For example, the appliance 70 includes a bracket structure 72 that is fixed to a pad 71. The bracket structure 72 includes tie wings 73 on the occlusal side thereof and tie wings 74 on the gingival side thereof. The outer surface 76 of the tie wing 73 is tapered toward the base 71 so that an impacting object (not shown) is deflected as indicated by the arrow 75. The base 71 may also be configured to provide a tapered protective barrier 77 that prevents the impacting object from engaging the occlusal tip 78 of the bracket tie wing 73. The tapered barrier 77 also provides ease of handling the appliance 70. While other surfaces of the appliance 70 may also be tapered, the avoidance of surfaces on the occlusal side of the appliance 70 most greatly reduces the likelihood of a blunt surface encountering an impacting object, since the greatest likelihood of an object impacting an orthodontic appliance is from the occlusal side of the appliance. This embodiment of the invention presents a feature that can be used most readily in combination with the features of the various embodiments described above.

Thus, exemplary embodiments of the orthodontic appliance of the present invention comprises an archwire support structure, such as a bracket, compliantly attached to a bonding structure or bonding base, such as a mesh, through attachment locations on a pad affixed to the base of the archwire support structure, or through attachment locations on the archwire support structure base itself. By providing resiliency and compliancy between the archwire support structure and the bonding base, the appliance, adhered to a tooth, is more resistant to impact and particularly to the shear and tensile forces which may be exerted upon it. Moreover, the appliance reduces the transfer of impacting energy in turn reducing the risk of debonding the bracket from the underlying tooth. Further embodiments resist impact by providing an archwire support structure comprised of elastic materials, by providing a bonding structure surrounded with an impact-absorbing elastomeric material, and/or by providing an adhesive having a substantially lower modulus of elasticity. To this end, the present invention improves the ability of the appliance to sufficiently decelerate impacting objects to reduce the risk of fracture of the underlying adhesive bond. Accordingly, the present invention provides a cost savings to the patient by requiring less repair, less visits to the orthodontist, and a more durable orthodontic appliance while overcoming many of the drawbacks of the prior art in terms of the potential and the degree of appliance failure during everyday activity.

While the present invention has been illustrated by the description of an embodiment thereof, and while the embodiment has been described in considerable detail, it is not intended to restrict or in any limit the scope of the appended claims to such detail. Additional advantages and modifications will readily appear to those skilled in the art. The invention in its broader aspects is, therefore, not limited to the specific details, representative apparatus and method, and illustrated examples shown and described. Accordingly, departures may be made from such details without departing from the scope or spirit of Applicant's general inventive concept.

What is claimed is:

1. An orthodontic appliance for attachment to a tooth, the appliance comprising:
    a bracket having a pad that includes an inner central portion and an outer peripheral portion contiguous with and in surrounding relation to the inner central portion; and
    a bonding structure configured to provide bonding of the bracket with adhesive to a tooth and compliantly attached to the bracket at a plurality of points around the perimeter of the outer peripheral portion of the pad and substantially free from attachment to the bracket at the inner central portion of the pad to provide compliant movement between the bracket and the bonding structure upon impact to the bracket, so as to resist transmission of impact from the bracket to the adhesive.

2. The orthodontic appliance of claim 1 wherein the bonding structure includes a mesh.

3. The orthodontic appliance of claim 1 wherein the outer peripheral portion comprises a metal sheet.

4. The orthodontic appliance of claim 3 wherein the metal sheet is a foil.

5. The orthodontic appliance of claim 1 wherein the bracket is a metal bracket.

6. The orthodontic appliance of claim 5 wherein the bonding structure is a wire mesh.

7. The orthodontic appliance of claim 5 wherein the bracket comprises a material selected from the group consisting of a metal, a ceramic and a plastic.

8. An orthodontic appliance for attachment to a tooth, the appliance comprising:
   a bracket having a pad attached thereto, the pad having thereon an outer peripheral portion and an inner central portion; and
   a mesh having an attachment to the outer peripheral portion around the perimeter thereof and encircling the inner central portion, and the mesh being substantially free from attachment to the inner central portion, the attachment providing compliant movement between the inner central portion and the mesh upon impact.

9. The orthodontic appliance of claim 8 wherein the bracket is formed of a material selected from the group consisting of a metal, a ceramic and a plastic.

10. The orthodontic appliance of claim 8 wherein the bracket and the mesh are each formed of metal and the attachment includes a weld joining the mesh to the pad around the outer peripheral portion.

11. The orthodontic appliance of claim 8 wherein the outer peripheral portion is contiguous with the inner central portion.

12. The orthodontic appliance of claim 8 wherein the pad is formed of a metal sheet having thereon the outer peripheral portion surrounding the inner central portion on one side of the sheet;
   the bracket includes archwire support structure fixed to the pad on one side thereof opposite the inner central portion; and
   the attachment including a weld of the mesh to the outer peripheral portion of the pad.

13. The orthodontic appliance of claim 12 wherein the pad is a foil.

* * * * *

UNITED STATES PATENT AND TRADEMARK OFFICE
CERTIFICATE OF CORRECTION

PATENT NO. : 7,331,782 B2
APPLICATION NO. : 10/734742
DATED : February 19, 2008
INVENTOR(S) : Craig A. Andreiko It is certified that error appears in the above-identified patent and that said Letters Patent is hereby corrected as shown below:

In column 1, line 10, "in dental applications, and in particular, to" should read --in dental applications, and, in particular, to--.

In column 1, line 37, "across the problematic areas, and in particular, across" should read --across the problematic areas, and, in particular, across--.

In column 7, line 54, "FIG. 8 is cross-sectional view" should read --FIG. 8 is a cross-sectional view--.

In column 8, line 11, "As shown in FIG. 2, the pad 14, is a component" should read --As shown in FIG. 2, the pad 14 is a component--.

In column 10, line 39, "each of which are attached to" should read --each of which is attached to--.

In column 11, line 37, "greater then that of" should read --greater than that of--.

In column 14, line 2, "of the present invention comprises" should read --of the present invention comprise--.

In column 14, line 34, "or in any limit the scope" should read --or in any way limit the scope--.

Signed and Sealed this

Twenty-fourth Day of February, 2009

JOHN DOLL
*Acting Director of the United States Patent and Trademark Office*